United States Patent [19]

Ishizaka

[11] Patent Number: 5,691,543
[45] Date of Patent: Nov. 25, 1997

[54] INSPECTING DEVICE AND METHOD FOR DETECTING MINUTE CONTOUR DEFECTS

[75] Inventor: Yutaka Ishizaka, Kawasaki, Japan

[73] Assignee: Fuji Electric Co., Ltd., Kawasaki, Japan

[21] Appl. No.: 460,498

[22] Filed: Jun. 2, 1995

[30]  Foreign Application Priority Data

Jun. 2, 1994 [JP] Japan ................... 6-121060

[51] Int. Cl.⁶ ................................................. G01N 21/88
[52] U.S. Cl. ....................... 250/559.06; 250/559.22; 382/141
[58] Field of Search .................. 250/559.06, 559.22, 250/559.23; 356/376; 382/141, 142, 152, 199

[56]  References Cited

U.S. PATENT DOCUMENTS 5,157,735 10/1992 Maeda et al. ................... 382/141
5,233,199  8/1993 Toyama .
5,268,968 12/1993 Yoshida ........................... 382/141
5,287,293  2/1994 Chen et al. ....................... 382/152

*Primary Examiner*—Edward P. Westin
*Assistant Examiner*—Kevin Pyo
*Attorney, Agent, or Firm*—Greer, Burns & Crain, Ltd.

[57]  ABSTRACT

A contour inspecting device for detecting a defect in a contour of an object to be inspected according to the invention comprises; an image memory for storing an image of the inspection object captured by a camera; a scanner for scanning, along a plurality of scanning lines, an inspection region which covers a part of the image stored in the image memory; a binary unit for converting an image signal read out by the scanner into a binary signal; a detector for detecting positions of changing points at which the value of the binary signal changes; a comparator for calculating a difference between positions of the changing points on two of the plurality of scanning lines separated from each other by a predetermined interval; and a decision unit for determining whether or not the contour of the inspection object has a defect on the basis of a comparison of the difference with a predetermined value.

15 Claims, 6 Drawing Sheets

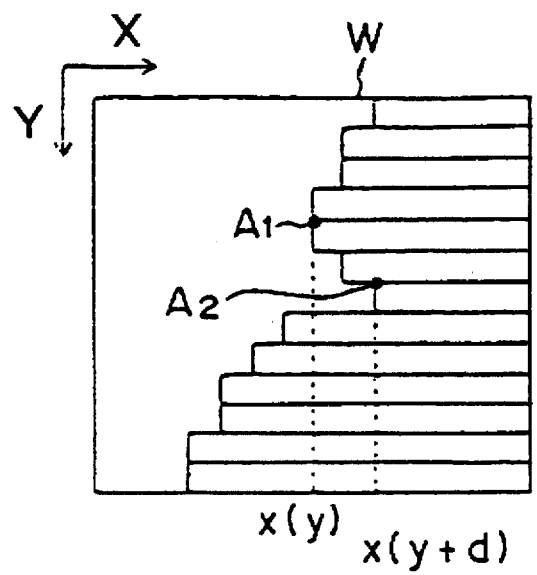
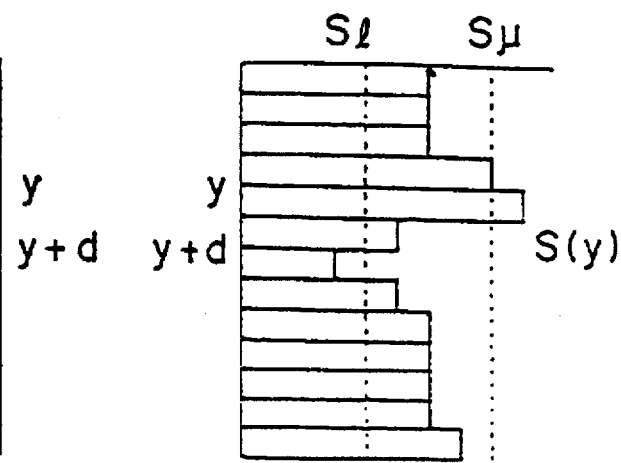
FIG. 6A  FIG. 6B
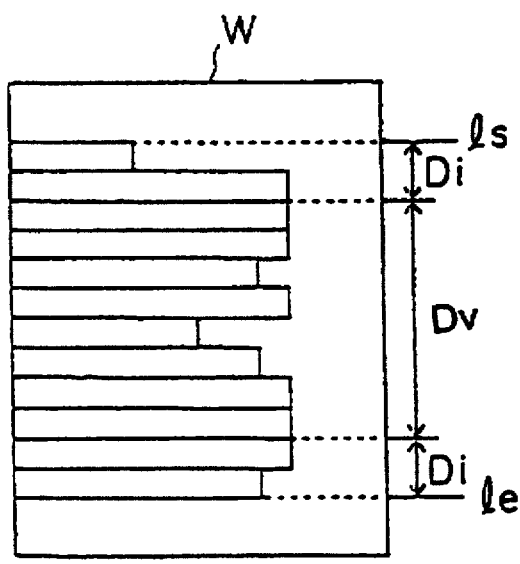
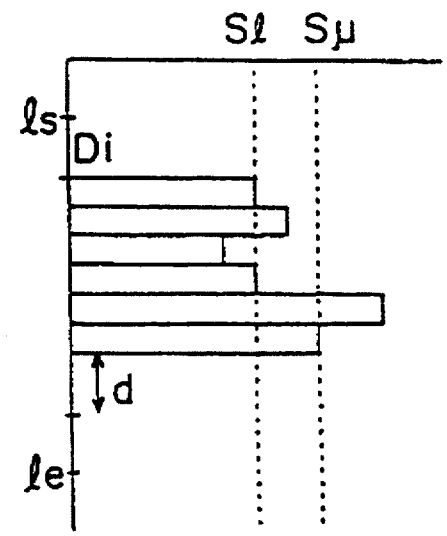
FIG. 7A  FIG. 7B

INSPECTING DEVICE AND METHOD FOR DETECTING MINUTE CONTOUR DEFECTS

BACKGROUND OF THE INVENTION

1. Field of the Invention

The present invention relates to a device for automatically inspecting appearance defects of products on a production line, and, more particularly, a device for inspecting defects in the contour or the profile of various kinds of the products.

2. Description of the Related Art

A conventional method for inspecting defects in the contour of a product comprises steps for providing an inspection region along the periphery of the product to be inspected, displaying the product as a binary image, and detecting contour defects of the product on the basis of a change in the area of the inspection region. The template-matching method is included in this conventional method.

FIG. 1 shows an inspection method according to a conventional contour inspecting device.

In this figure, Pa represents a pattern to be inspected, Wa a ring-shaped inspection region arranged outside the pattern Pa, and Wb another ring-shaped inspection region arranged inside the pattern Pa. The outer inspection region Wa is used for detecting a defect portion Fa1 projecting outward from the pattern Pa, which is usually called "flash", while the inner inspection region Wb is used for detecting a chipped portion Fb1. The conventional pattern contour inspecting device detects contour defects in the pattern on the basis of a change in the area of the outer inspection region Wa caused by the flash Fa1 of the pattern Pa, and a change in the area of the inner inspection region Wb caused by the chipped portion Fb1 of the pattern Pa.

In the above described method, however, a non-inspection region Wc provided between the outer inspection region Wa, and the inner inspection region Wb, is required in order to avoid influences caused by quantization errors, caused by a difference in the shape or the size of the pattern from a standard value, and caused by a difference in position of the pattern from a specified position. According to the conventional method, therefore, defects smaller than the width of the non-inspection region Wc cannot be detected. A minute flash Fa2 and a minute chipped portion Fb2 shown in FIG. 1, for example, cannot be detected, because they do not change the area of the inner inspection region Wb or the area of the outer inspection region Wa.

SUMMARY OF THE INVENTION

The object of the present invention is therefore to provide a device and a method capable of detecting minute defects in the contour of an object (or a pattern) to be inspected, and, more particularly, to provide a device and a method capable of correctly detecting such minute defects even when the size or the shape of the object is different from the standard values, and when the object is shifted from its predetermined inspection position.

The contour inspecting device for detecting a defect in a contour of an object to be inspected, according to the present invention, comprises; an image memory for storing an image of the object captured by a camera; a scanner for scanning, along a plurality of scanning lines, an inspection region which covers at least a part of the image stored in the image memory; a binary unit for converting an image signal read out by the scanner into a binary signal; a detector for detecting positions of changing points at which the value of the binary signal changes; a comparator for calculating a difference between positions of two of the changing points on two of the scanning lines separated from each other by a predetermined distance; and a decision unit for deciding whether or not the object has a defect in its contour on the basis of a result obtained by comparing this difference with a predetermined value.

The contour inspecting method for detecting a defect in a contour of an object to be inspected, according to the present invention, comprises the steps of; storing an image of the object captured by a camera in an image memory; scanning along a plurality of scanning lines, by a scanner, an inspection region which covers at least a part of the image stored in the image memory; converting an image signal read out by the scanner into a binary signal by a binary unit; detecting positions of changing points at which the value of the binary signal changes on the plurality of scanning lines, by a detector; calculating a difference between the positions of two of the changing points on two of the scanning lines separated from each other by a predetermined distance, by a comparator; and deciding whether or not the object has a defect in its contour, by a decision unit, on the basis of a result obtained by comparing the difference calculated with a predetermined value.

The scanner may scan the inspection region along one of a horizontal direction and a vertical direction, the binary signal may be obtained by converting the image signals into two values of "0" and "1", and the changing point may be a point at which the binary signal changes from "0" to "1" or from "1" to "0".

When a scanning line along which no changing point is detected is present in the inspection region, the comparator may not calculate the difference for a predetermined number of scanning lines counted from the first and the last of scanning lines along which changing points are detected, and may calculate the difference for the remaining scanning lines.

When a scanning line along which no changing point is detected is present in the inspection region, the comparator may omit calculating the difference for scanning lines which are included in a predetermined range counted from the first and the last of scanning lines along which changing points are detected, and may calculate the difference for the remaining scanning lines.

The predetermined distance between two scanning lines may be set corresponding to at least one of the size and the shape of a defect to be detected. Further, the predetermined value may be set corresponding to at least one of the size and the shape of a defect to be detected.

According to the present invention, therefore, minute defects in the contour of the object can be correctly detected even when the size or the shape of the object is different from the standard values and when the object is shifted from its predetermined inspection position. Further, the contour of the object can be correctly detected with precision because the influence of quantization errors,in the contour inspection can be significantly reduced.

BRIEF DESCRIPTION OF THE DRAWINGS

FIGS. 6A and 6B show how the contour of the object is decided and checked according to the embodiment of the present invention.

FIGS. 7A and 7B show how the contour of the object is decided and checked according to the embodiment of the present invention.

DETAILED DESCRIPTION OF THE PREFERRED EMBODIMENT

A contour inspecting device according to the present invention will be described below.

Figure 1:
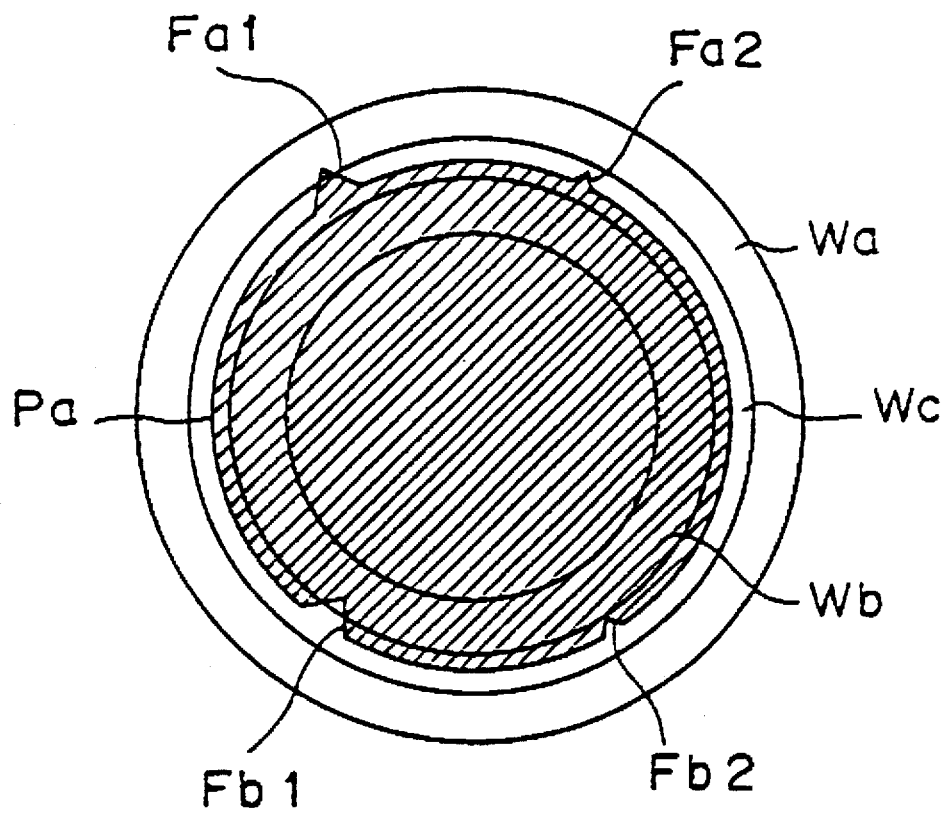
FIG. 1 shows a contour inspecting method according to the conventional pattern contour inspecting device.
Figure 2:
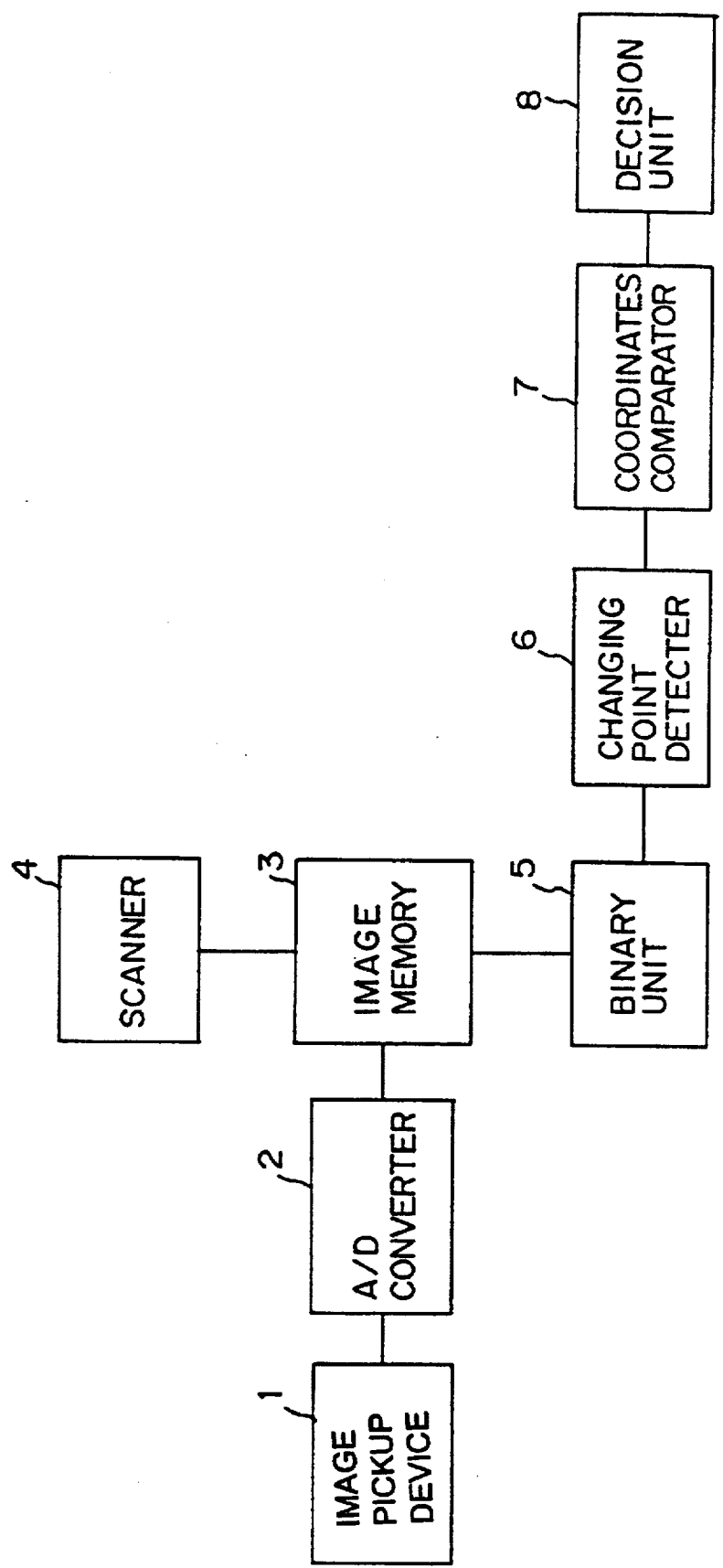
FIG. 2 shows a configuration of an embodiment of a contour inspecting device according to the present invention.

As shown in FIG. 2, the contour inspecting device comprises an image pickup device 1, such as a camera, an A/D (analog/digital) converter 2, an image memory 3, a scanner 4, a binary unit 5, a changing point detector 6, a coordinates comparator 7, and a decision unit 8. These components are realized by hardware, but some of them may be realized by software.

The image pickup device 1 picks up an object to be inspected, such as a pattern, as an analog image, and the A/D converter 2 converts the analog image sent from the image pickup device 1 to a digital image. The image memory 3 stores the digital image sent from A/D converter 2, and the scanner 4 scans all regions or a part of the digital image stored in the image memory 3 along scanning lines in a horizontal or vertical direction, and sends the contents of the digital image thus scanned to the binary unit 5.

The binary unit 5 converts the contents of the image read out from the image memory 3 by the scanner 4, into a binary signal having values of either "0" or "1". The changing point detector 6 searches the binary signal, and if it detects a changing point on each of the scanning lines, determines the coordinates of the changing point, which include the rising point and the falling point. The "rising point" denotes a point at which the signal changes from "0" to "1", and the "falling point" denotes a point at which the signal changes from "1" to "0". One of the rising and falling points may be on the scanning lines in some cases, but both of them or neither of them may be on the scanning lines in other cases.

The coordinates comparator 7 compares the coordinates of the changing points obtained by the changing point detector 7, to get a difference in the position of the changing points. In this embodiment, the coordinates comparator 7 calculates the difference of coordinates of the changing points on two scanning lines which are separated from each other by a predetermined distance. The decision unit 8 compares the difference of coordinates of these changing points calculated by the coordinates comparator 7 with a predetermined value to determine whether or not the object has a defect in its profile.

Scanning regions used in a contour inspecting method of the present invention will be described below.

Figure 3:
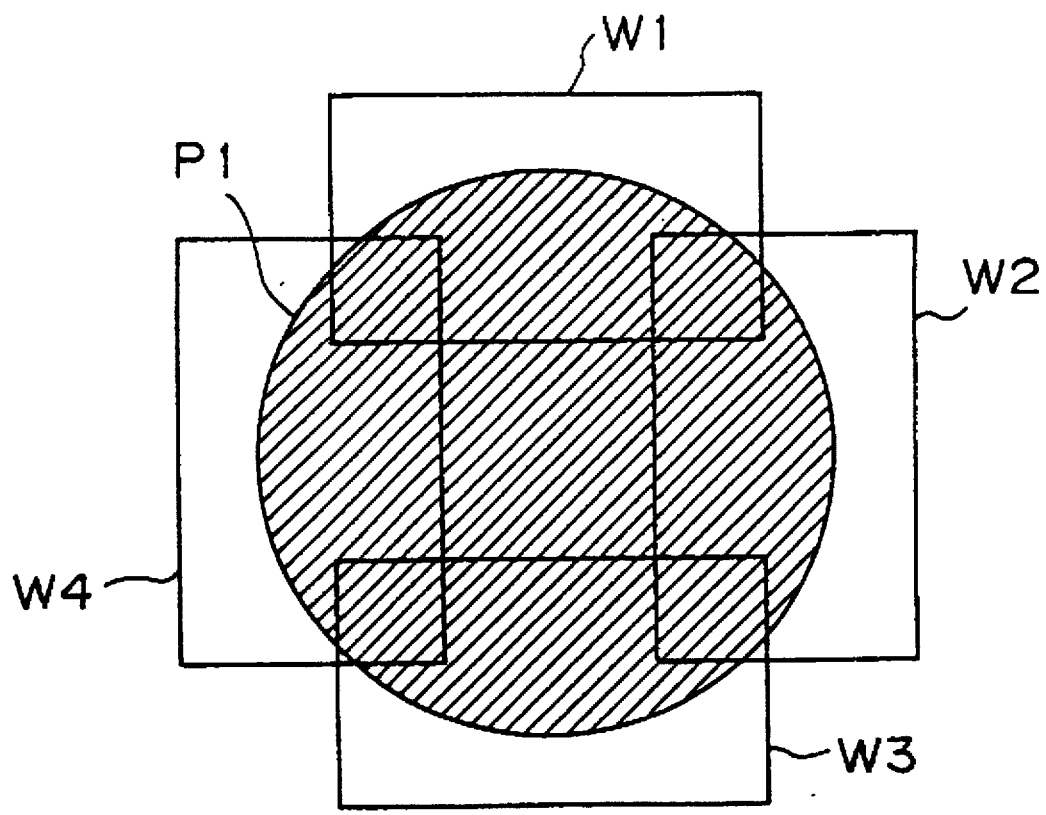
FIG. 3 shows a contour inspecting method according to the embodiment.

In FIG. 3, reference numeral P1 represents the image of the object stored in the image memory 3, and W1, W2, W3 and W4 denote scanning regions to be scanned by the scanner 4. Since the entire circumference of the object P1 is covered by the scanning regions W1–W4, the entire circumference of the object P1 is inspected by scanning the scanning regions W1–W4.

Figure 4A:
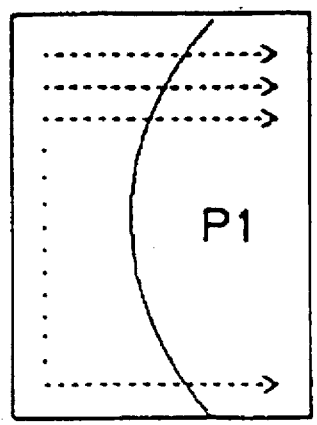
FIGS. 4A and 4B show a scanning method for an object being inspected according to the contour inspecting method.
Figure 4B:
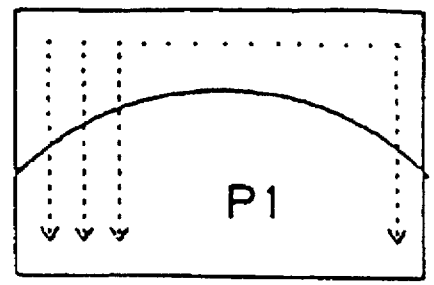

Referring to FIGS. 4A and 4B, it will be described how the scanning regions W1–W4 are scanned.

FIG. 4A shows how the scanning regions W2 and W4 shown in FIG. 3 are scanned, and FIG. 4B shows how the other scanning regions W1 and W3 are scanned. The scanning regions W2 and W4 cover the right and left parts of the circumference of the object P1, and are scanned in the horizontal direction, as shown by dotted arrows in FIG. 4A. On the basis of this scanning, changing points corresponding to the right and left sides of the object P1 are detected. The scanning regions W1 and W3 cover the top and bottom parts of the circumference of the object P1, and are scanned in the vertical direction, as shown by dotted arrows in FIG. 4B. On the basis of this scanning, changing points corresponding to the top and bottom parts of the object P1 are detected.

Since the scanning regions W1–W4 are arranged relative to the object P1 as shown in FIG. 3, the direction in which the scanning regions W2 and W4 are scanned is therefore shifted from the direction in which the scanning regions W1 and W3 are scanned by approximately 90°. Changing points in the scanning regions W1 and W4 are detected as the rising points, while changing points in the scanning regions W2 and W3 are detected as the falling points. The contour line of the object P1 is determined on the basis of rising and falling points thus detected.

Another scanning method for an object P2, which is different in shape from the object P1 shown in FIG. 3, will be described below.

Figure 5:
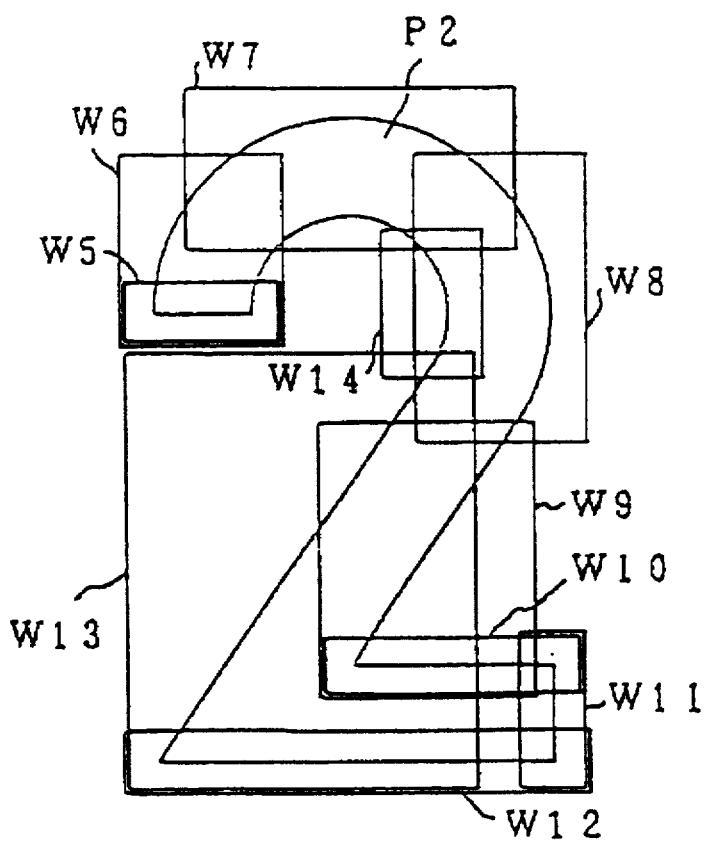
FIG. 5 shows another contour inspecting method using an object different from the object shown in FIG. 3.

Scanning regions W5, W6, W7, W8, W9, W10, W11, W12, W13 and W14 are arranged for the object P2, as shown in FIG. 5. Since the entire periphery of the object target P2 is covered by the scanning regions W5–W14, the complete contour line of the object P2 is inspected by scanning the scanning regions W5–W14 in the horizontal or vertical direction.

Referring to FIGS. 6A and 6B, the methods of determining the coordinates of the changing point and the contour line of the object will be described below.

FIG. 6A shows image data obtained by the scanning of a scanning region W and converted by the Binary unit 5. X and Y in FIG. 6A represent axes of coordinates by which the coordinates of the changing point are determined. FIG. 6A shows image data obtained by scanning in the horizontal direction, which is along the X axis. FIG. 6A also shows that a scanning line scanning a position of y in the direction of the Y axis (Y=y) has detected a rising point A1(x(y), y) at a position of x(y) in the direction of the X axis (X=x(y)), and that the scanning line scanning a position of y+d in the direction of the Y axis (Y=y+d) has detected another rising point A2 (x(y+d), y+d) at a position of x(y+d) in the direction of the X axis (X=x(y+d)) On the basis of the coordinates of the changing points detected by these scanning lines, inclinations of the contour line or position difference of two points in the contour line of the object are calculated by the coordinates comparator 7.

The inclinations of the contour line thus calculated by the coordinates comparator unit 7 are shown in FIG. 6B, corresponding to each scanning line. An inclination S(y) of the contour line (or a difference S(y) of changing points in the direction of the axis X) at the position of y the Y axis will be obtained from the following equation (1).

$$S(y)=x(y+d)-x(y) \qquad (1)$$

wherein x(y) represents an X co-ordinate of the changing point detected by the scanning line at the position of y. The value of an interval d between the two scanning lines used to obtain the inclination S(y) is determined in accordance with the size and the shape of the defects to be detected.

The inclination S(y) corresponding to the scanning line scanning the position of y in the Y axis is compared with a minimum threshold value S1 which denotes the lower limit of a predetermined correct inclination range, and also with a maximum threshold value Su which denotes the upper limit of the range. If the inclination S(y) meets the following relation (2), the decision unit 8 determines that the object has a defect in its contour at the position of y in the Y direction.

$$S(y)<S1 \text{ or } S(y)>Su \tag{2}$$

According to the above-described embodiment, since the defect is detected on the basis of the difference in the coordinates of the changing point, which represents the contour line of the object, even when the size and the shape of the object are different from their reference values, and when the contour line of the object is shifted from its predetermined inspection position, no influence is exerted on the difference in the coordinates of a changing point, and the contour inspection can be conducted using a single pair of threshold values.

In the inspection according to the above-described embodiment, a scanning region in which scanning lines along which no changing point is detected even when scanning is made in the horizontal or vertical direction, for example a scanning region W5, W6, W10, W11, W12, or W14 in FIG. 5, may exist. When such a region is scanned, one end or both ends of a range in which the changing point is detected may be changed by the influences caused by quantization errors and shifting of the inspection target from its predetermined position. Because of this change, in the end of the range, inspection results obtained in a portion adjacent to the first or the last scanning line on which the changing point is detected become unstable.

FIGS. 7A and 7B show a determination method for eliminating the above-mentioned drawback.

ls in FIG. 7A denotes a first scanning line of scanning lines in which the changing point is detected in the scanning region W, and le denotes the last scanning line of such scanning lines. According to the decision method, scanning lines included in a predetermined distance Di after the first scanning line ls, and scanning lines included in the predetermined distance Di before the last scanning line le, are removed and not used to calculate inclinations of the contour line of the object. Therefore, inclinations are calculated using changing points detected by the remaining scanning lines included in a range Dv.

FIG. 7B shows inclinations thus obtained corresponding to each of the scanning lines. As shown in FIG. 7B, inclinations are calculated after subtraction of the scanning lines included in a predetermined distance after the first of the changing point detecting scanning lines, and those included in the predetermined distance before the last of the changing point detecting scanning lines, from the whole range of changing point detecting scanning lines. In other words, after removing a predetermined number of scanning lines from all of the scanning lines in which changing points are detected, the inclinations are calculated. As a result, inclinations are calculated for scanning lines in a portion remaining after subtraction of, for example, the interval d from the portion indicated by the distance Dv.

When scanning regions, such as regions W1–W4 in FIG. 3 or regions W6–W8 in FIG. 5, cover curved portions of the contour of an object, inclinations obtained are changed for every scanning line. For these scanning regions, the threshold values Sl and Si may be set for every scanning line. Further, this scanning region can be divided into a plurality of decision regions, and the threshold values Sl an Si can be set for every decision region. When the comparison values are thus changed according to the inspection position, any defect of the object can be detected with a high degree of accuracy.

Figures 8A, 8B:
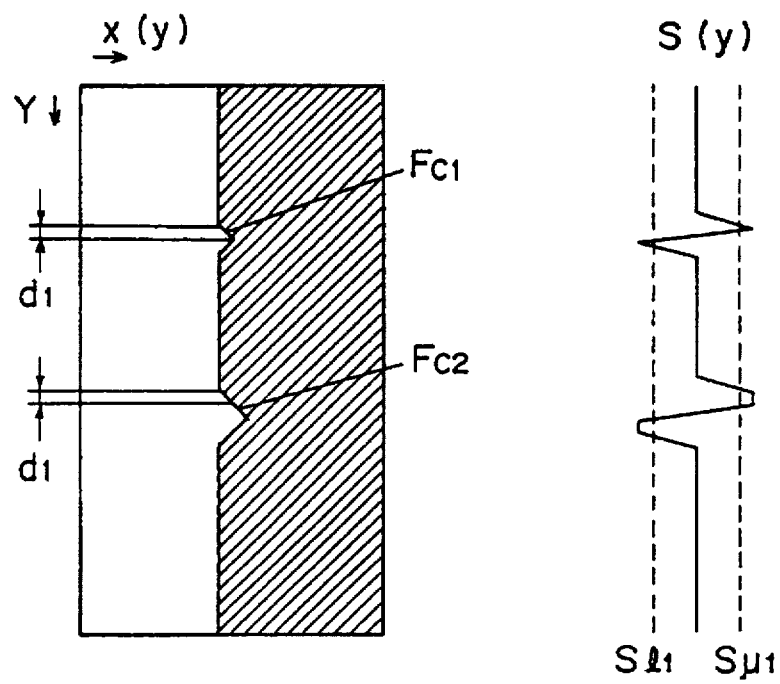
FIGS. 8A and 8B show how defects in the contour of the object are detected according to the embodiment of the present invention.
Figures 9A, 9B:
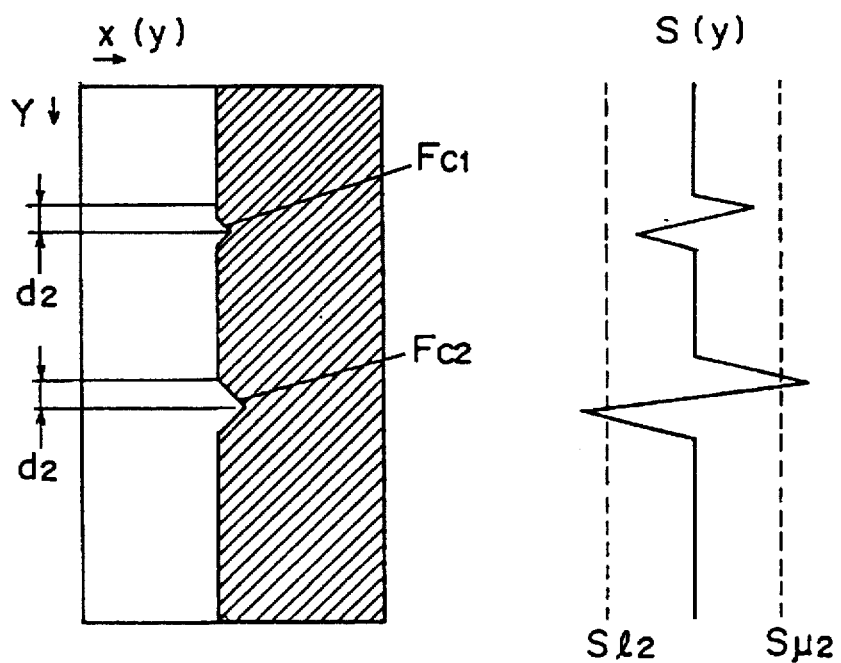
FIGS. 9A and 9B also show how defects in the contour of the object are detected according to the embodiment of the present invention.

Referring to FIGS. 8A, 8B, 9A and 9B, a method of setting of the interval d according to the defect detection will be described below. Fc1 and Fc2 in FIGS. 8A and 9A denote defects in the contour of an object. The defect Fc2 has a width two times larger than that of the defect Fc1. FIGS. 8B and 9B show inclinations S(y) obtained by the detection method shown in FIGS. 8A and 9A.

In the inspection shown in FIG. 8A the value of the interval d is set to be d1 which is approximately half the width of defect Fc1. When a determination is made on the basis of inclinations obtained by this inspection, the defects Fc1 and FC2 are shown by inclinations having substantially the same value, as shown in FIG. 8B. When the larger defect Fc2 is determined as a defect according to the threshold values Sl1 and Su1, the smaller defect Fc1 is also determined as a defect.

In the inspection shown in FIG. 9A, the value of the interval d is set to be a value d2 which is approximately two times the interval d1 and substantially the same as the full width of the defect Fc1. When a determination is made on the basis of inclinations obtained by this inspection, an inclination obtained from the larger defect Fc2 has a value approximately two times the value of an inclination obtained from the smaller defect Fc1. In this case, even if the larger defect Fc2 is determined as a defect according to the comparison values Sl2 and Su2, the smaller defect Fc1 is not detected as a defect.

As described above, the interval d can be set corresponding to the smallest defect to be detected, so that negligible minute defects can be excluded from the inspection, and defects can be detected to a desired accuracy.

What is claimed is:

1. A contour inspecting device for detecting a defect of a contour of an object to be inspected, comprising:

an image storing means for storing an image of the object to be inspected captured by an image pick up means;

a scanning means for scanning, along a plurality of scanning lines, an inspection region which covers at least a part of the image stored in the image storing means;

a binary means for converting an image signal read out by the scanning means into a binary signal;

a detecting means for detecting positions of changing points at which the value of the binary signal changes on the plurality of scanning lines;

a comparing means for calculating an inclination between changing points on two of said plurality of scanning lines separated from each other by a predetermined interval; and a decision means for deciding whether or not the contour of the inspection object has a defect on the basis of a comparison of said inclination with a specified value.

2. The contour inspecting device according to claim 1, wherein, when a scanning line along which no changing point is detected is present in the inspection region, the comparing means does not calculate an inclination between changing points on a predetermined number of scanning lines from the first and last of said scanning lines of a scanning region.

3. The contour inspecting device according to claim 1, wherein said predetermined interval is set corresponding to at least one of a size and a shape of a defect to be detected.

4. The contour inspecting device according to claim 1, wherein said specified value is set corresponding to at least one of a shape and a size of a defect to be detected.

5. The contour inspecting device according to claim 1, wherein said binary signal is formed by converting the image signal into values of either "0" or "1", and said changing point is one of a point at which said binary signal changes from "0" to "1" and a point at which said binary signal changes from "1" to "0".

6. The contour inspecting device according to claim 1, wherein said scanning means scans the inspection region along one of the horizontal and vertical axes.

7. The contour inspecting device according to claim 1, wherein said comparing means calculates the inclination between changing points on scanning lines within a region bounded by a predetermined number of scanning lines from the first and last scanning lines of the inspection region.

8. A contour inspection method for detecting a defect in the contour of an inspection object, comprising the steps of:

storing an image of the inspection object;

scanning, along a plurality of scanning lines, an inspection region which covers at least a part of the image;

converting an image signal read out by scanning the inspection region into a binary signal;

detecting positions of changing points on said plurality of scanning lines at which the value of the binary signal changes;

calculating the inclination between positions of the changing points on two of said plurality of scanning lines separated from each other by a predetermined interval; and deciding whether or not the contour of the inspection object has a defect on the basis of a comparison of said inclination with a specified value.

9. The contour inspection method according to claim 8, wherein when a scanning line on which no changing point is detected is present in the inspection region, said inclination is not calculated for a predetermined number of scanning lines from the first and last of said scanning lines along which changing points are detected.

10. The contour inspection method according to claim 8, wherein said predetermined interval is set corresponding to at least one of a size and a shape of a defect to be detected.

11. The contour inspection method according to claim 8, wherein said specified value is set corresponding to at least one of a size and a shape to a defect to be detected.

12. The contour inspection method according to claim 8, wherein said binary signal is formed by converting the image signal into values of either "0" or "1", and the changing point is one of a point at which the binary signal changes from "0" to "1" and a point at which the binary signal changes from "1" to "0".

13. The contour inspection method according to claim 8, wherein the inspection region is scanned along one of horizontal and vertical directions.

14. The contour inspection method according to claim 8, wherein said inclination is calculated for scanning lines included in a range in the inspection region.

15. The contour inspection method according to claim 8, wherein said inclination is calculated for scanning lines included in a predetermined range within a region bounded by a predetermined number of scanning line from the first and last of said scanning lines along which changing points are detected in the inspection region.

* * * * *

UNITED STATES PATENT AND TRADEMARK OFFICE
CERTIFICATE OF CORRECTION

PATENT NO. : 5,691,543
DATED : Nov 25, 1997
INVENTOR(S) : Sakata

It is certified that error appears in the above-identified patent and that said Letters Patent is hereby corrected as shown below:

Under "[57] Abstract", line 3, delete "comprises;" and insert --comprises--.

Column 1, line 60, delete "comprises;" and insert --comprises:-- therefor.

Column 4, line 65, delete "of y the Yaxis" and insert --of y in the Yaxis-- therefor.

Column 5, line 14, delete "S(y) < S1" and insert --S(y) < S$1$-- therefor.

Column 5, line 20, delete "values, ahd" and insert --values, and-- therefor.

Column 5, line 41, delete "Is in FIG. 7A" and insert --$1$s in FIG. 7A-- therefor.

UNITED STATES PATENT AND TRADEMARK OFFICE
CERTIFICATE OF CORRECTION

PATENT NO. : 5,691,543
DATED : Nov 25, 1997
INVENTOR(S) : Sakata

It is certified that error appears in the above-indentified patent and that said Letters Patent is hereby corrected as shown below:

Column 5, line 43, delete "le denotes" and insert --*l*e denotes-- therefor.

Column 5, line 46, delete "ls, and" and insert --*l*s, and -- therefor.

Column 5, line 47, delete "line 1e," and insert --line *l*e,-- therefor.

Column 6, line 3, delete "values S1" and insert --values S*l*-- therefor.

Column 6, line 3, delete "Si may" and insert --S*u* may-- therefor.

UNITED STATES PATENT AND TRADEMARK OFFICE
CERTIFICATE OF CORRECTION

PATENT NO. : 5,691,543
DATED : Nov 25, 1997
INVENTOR(S) : Sakata

It is certified that error appears in the above-indentified patent and that said Letters Patent is hereby corrected as shown below:

Column 6, line 5, delete "values S1" and insert --values S*1*-- therefor.

Column 6, line 5, delete "an Si can" and insert --and S*u* can-- therefor.

Column 6, line 21, delete "and FC2 are" and insert --and Fc2 are-- therefor.

Column 6, line 24, delete "Sl1 and Su1" and insert --S*1*1 and S*u*1-- therefor.

UNITED STATES PATENT AND TRADEMARK OFFICE
CERTIFICATE OF CORRECTION

PATENT NO. : 5,691,543
DATED : Nov 25, 1997
INVENTOR(S) : Sakata

It is certified that error appears in the above-indentified patent and that said Letters Patent is hereby corrected as shown below:

Column 6, line 35, delete "S12 and Su2" and insert --S$l$2 and S$u$2-- therefor.

Column 8, line 33, delete "scanning line from" and insert --scanning lines from--.

Column 8, line 16, delete "shape to a" and insert --shape of a--.

Signed and Sealed this

First Day of September, 1998

BRUCE LEHMAN

*Attest:*

*Attesting Officer*     *Commissioner of Patents and Trademarks*

UNITED STATES PATENT AND TRADEMARK OFFICE
CERTIFICATE OF CORRECTION

PATENT NO. : 5,691,543
DATED : November 25, 1997
INVENTOR(S) : Yutaka Ishizaka

It is certified that error appears in the above-identified patent and that said Letters Patent is hereby corrected as shown below:

Under "[57] Abstract", line 3, delete "comprises;" and insert --comprises--.

Column 1, line 60, delete "comprises;" and insert --comprises:-- therefor.

Column 4, line 65, delete "of y the Yaxis" and insert --of y in the Yaxis-- therefor.

Column 5, line 14, delete "S(y) < S1" and insert --S(y) < S$l$-- therefor.

Column 5, line 20, delete "values, ahd" and insert --values, and-- therefor.

Column 5, line 41, delete "Is in FIG. 7A" and insert --$l$s in FIG. 7A-- therefor.

UNITED STATES PATENT AND TRADEMARK OFFICE
CERTIFICATE OF CORRECTION

PATENT NO. : 5,691,543
DATED : November 25, 1997
INVENTOR(S) : Yutaka Ishizaka

It is certified that error appears in the above-indentified patent and that said Letters Patent is hereby corrected as shown below:

Column 5, line 43, delete "le denotes" and insert --$l$e denotes-- therefor.

Column 5, line 46, delete "ls, and" and insert --$l$s, and -- therefor.

Column 5, line 47, delete "line le," and insert --line $l$e,-- therefor.

Column 6, line 3, delete "values S1" and insert --values S$l$-- therefor.

Column 6, line 3, delete "Si may" and insert --S$u$ may-- therefor.

UNITED STATES PATENT AND TRADEMARK OFFICE
CERTIFICATE OF CORRECTION

PATENT NO. : 5,691,543
DATED : November 25, 1997
INVENTOR(S) : Yutaka Ishizaka

It is certified that error appears in the above-indentified patent and that said Letters Patent is hereby corrected as shown below:

Column 6, line 5, delete "values S1" and insert --values S$l$-- therefor.

Column 6, line 5, delete "an Si can" and insert --and S$u$ can-- therefor.

Column 6, line 21, delete "and FC2 are" and insert --and Fc2 are-- therefor.

Column 6, line 24, delete "Sl1 and Su1" and insert --S$l$1 and S$u$1-- therefor.

UNITED STATES PATENT AND TRADEMARK OFFICE
CERTIFICATE OF CORRECTION

PATENT NO. : 5,691,543
DATED : November 25, 1997
INVENTOR(S) : Yutaka Ishizaka

It is certified that error appears in the above-indentified patent and that said Letters Patent is hereby corrected as shown below:

Column 6, line 35, delete "S12 and Su2" and insert --S*12* and S*u*2-- therefor.

Column 8, line 33, delete "scanning line from" and insert --scanning lines from--.

Column 8, line 16, delete "shape to a" and insert --shape of a--.

This certificate supersedes Certificate of Correction issued September 1, 1998.

Signed and Sealed this

First Day of December, 1998

Attest:

BRUCE LEHMAN

*Attesting Officer*     *Commissioner of Patents and Trademarks*